US010782291B2

(12) United States Patent
Kircher et al.

(10) Patent No.: US 10,782,291 B2
(45) Date of Patent: Sep. 22, 2020

(54) CHROMOGENIC MEDIUM FOR THE DETECTION AND IDENTIFICATION OF VANCOMYCIN RESISTANT ENTEROCOCCI AND METHOD THEREFOR

(75) Inventors: Susan Kircher, Reisterstown, MD (US); Jon E. Salomon, Stewartstown, PA (US); Sheryl Douglas-Mckay, Baltimore, MD (US)

(73) Assignee: BECTON DICKINSON AND COMPANY, Franklin Lakes, NJ (US)

( * ) Notice: Subject to any disclaimer, the term of this patent is extended or adjusted under 35 U.S.C. 154(b) by 2776 days.

(21) Appl. No.: 11/958,827

(22) Filed: Dec. 18, 2007

(65) Prior Publication Data

US 2008/0145881 A1 Jun. 19, 2008

Related U.S. Application Data

(60) Provisional application No. 60/875,669, filed on Dec. 19, 2006.

(51) Int. Cl.
*C12Q 1/04* (2006.01)
*G01N 33/569* (2006.01)

(52) U.S. Cl.
CPC ..... *G01N 33/569* (2013.01); *G01N 2333/335* (2013.01)

(58) Field of Classification Search
CPC ......... G01N 33/569; C12Q 1/045; C12Q 1/04
See application file for complete search history.

(56) References Cited

U.S. PATENT DOCUMENTS

| | | | |
|---|---|---|---|
| 3,830,700 A | 8/1974 | O'callaghan et al. | |
| 4,925,789 A | 5/1990 | Edberg | |
| 5,210,022 A | 5/1993 | Roth et al. | |
| 5,358,854 A | 10/1994 | Ferguson | |
| 5,510,243 A | 4/1996 | Boyd et al. | |
| 5,610,029 A | 3/1997 | Ehrenfeld et al. | |
| 5,620,865 A | 4/1997 | Chen et al. | |
| 6,340,573 B1 | 1/2002 | Armstrong et al. | |
| 6,350,588 B1 | 2/2002 | Roth et al. | |
| 6,355,449 B1 | 3/2002 | Chen et al. | |
| 7,018,807 B2 | 3/2006 | Chen et al. | |
| 2002/0132285 A1 | 9/2002 | Chen et al. | |
| 2004/0121404 A1 | 6/2004 | Cotte et al. | |
| 2005/0112718 A1 | 5/2005 | Nakano et al. | |
| 2006/0014230 A1 | 1/2006 | Murata | |
| 2008/0145879 A1 | 6/2008 | Orenga et al. | |

FOREIGN PATENT DOCUMENTS

| | | |
|---|---|---|
| EP | 0059645 | 9/1982 |
| EP | 451775 | 10/1991 |
| EP | 1325923 | 7/2003 |
| EP | 1557473 | 7/2005 |
| JP | 2000316597 | 11/2000 |
| WO | 9212257 | 7/1992 |
| WO | 9219763 | 11/1992 |
| WO | 9504157 | 2/1995 |
| WO | 9615435 | 5/1996 |
| WO | 9804674 | 2/1998 |
| WO | 9909207 | 2/1999 |
| WO | 0224707 | 3/2002 |
| WO | 2004027086 | 4/2004 |
| WO | 2004040008 | 5/2004 |
| WO | 2004058995 | 7/2004 |
| WO | 2004063391 | 7/2004 |
| WO | 2005042770 | 5/2005 |
| WO | 2006085027 | 8/2006 |

OTHER PUBLICATIONS

Edberg et al., Rapid Detection of Vancomycin-Resistant Enterococci, Journal of Clinical Microbiology, 1994, vol. 32, No. 9, p. 2182-2184.*
Vincent et al., Vancomycin Resistance in Enterococcus gallinarum, Antimicrobial Agents and Chemotherapy, Jul. 1992, vol. 36, p. 1392-1399.*
Hanson et al., Comparison of Simple and Rapid Methods for identifying Enterococci Intrinsically resistant to vancomycin, Journal of Clinical Microbiology, 1999, vol. 37, p. 815-817.*
Panosian, K. et al., "Rapid Indentification of *Streptococcus bovis* by Using Combination Constitutive Enzyme Substrate Hydrolyses" Journal of Clinical Microbiology, Washington, DC, US, vol. 27, No. 8, pp. 1719-1722, Aug. 1989.
Van Horn et al., Journal of Clinical Microbiology, 34(4); 924-927 (1996).
Edberg et al., Journal of Clinical Microbiology, 32(9); 2182-2184 (1994).
International Search Report, PCT/US07/25969, dated Apr. 9, 2008.

* cited by examiner

*Primary Examiner* — Taeyoon Kim
*Assistant Examiner* — Tiffany M Gough
(74) *Attorney, Agent, or Firm* — Botos Churchill IP Law LLP

(57) ABSTRACT

A microbe-specific medium, containing specific chromogenic substrates, for the detection of vancomycin-resistant enterococci in a biological sample, whereby both the detection and identification of vancomycin-resistant enterococci at the species level is achieved utilizing one sample and one test.

18 Claims, 3 Drawing Sheets

CHROMOGENIC MEDIUM FOR THE DETECTION AND IDENTIFICATION OF VANCOMYCIN RESISTANT ENTEROCOCCI AND METHOD THEREFOR

CROSS REFERENCE TO RELATED APPLICATION

This application claims the benefit of the filing date of U.S. Provisional Patent Application No. 60/875,669 filed Dec. 19, 2006, the disclosure of which is incorporated herein by reference.

BACKGROUND OF THE INVENTION

The invention relates generally to a medium suitable for the detection and identification of Vancomycin-resistant enterococci.

Enterococci are normal inhabitants of the gastrointestinal (GI) tract of humans and most animals. They are widespread in nature and can be found in soil, water and vegetation. Depending on geographic location, the predominant species inhabiting the GI tract is either *Enterococcus faecalis* or *E. faecium*. Colonization with these organisms often precedes infection, including infection of the urinary tract, intra-abdominal cavity, and the lining of the heart (i.e., endocarditis).

Enterococci are resistant to many antibiotics, and the current treatment of choice is often vancomycin. However, enterococci have begun to develop resistance to it as well. These vancomycin-resistant strains of enterococci (VRE) have been associated with increased mortality.

There are two types of vancomycin resistance. One is intrinsic, the other is acquired. Intrinsic resistance is encoded by the vanC genes, and is not transferable. Intrinsic resistance is most commonly seen in *E. casseliflavus* and *E. gallinarum*. By contrast, acquired resistance, encoded by either the vanA or vanB genes, can be transferred and is commonly seen in *E. faecium* and *E. faecalis*. The species of enterococci associated with acquired resistance, are a cause for concern.

VRE were first reported in Europe in 1988 and in the United States in 1989. There has been a rapid increase in the incidence of VRE infection and colonization since then. Detection of VRE in the healthcare setting is a major challenge. The current CDC guidelines recommend the screening of stool or rectal swabs in the health care setting in order to identify patients who are positive for VRE. Further, once VRE is identified, it is recommended that the affected patient be placed in isolation. This practice enables containment of the transferable resistance genes. Placing all VRE positive patients in isolation as soon as possible reduces the risk of vanA and vanB gene transfer. However, not all enterococcal species that have elevated minimum inhibitory concentrations (MIC) to vancomycin possess a transferable resistant gene. Thus being able to distinguish among the species will prevent the unwarranted isolation and associated costs of those patients that test positive for *E. casseliflavus* or *E. gallinarum* (these typically possess the intrinsic resistance conferred by the vanC gene) versus *E. faecium* or *E. faecalis* (these typically possess the transferable resistance conferred by the vanA and/or vanB genes). *E. casseliflavus* and *E. gallinarum* are not epidemiologically significant as compared to *E. faecium* or *E. faecalis*.

Currently, several methods for detecting VRE are available. Some methods allow for the identification of VRE at the species level while others detect only the genus, or groups of species within the genus. Some methods utilize biological samples obtained directly from the source (e.g., a patient's stool), while others require a pure isolate from the initial sample before any identification can be made. For example, to obtain a pure isolate from a patient specimen additional processing, such as isolation to a secondary medium, may be necessary. Once a pure isolate has been obtained identification and or susceptibility testing can be performed. Methods for obtaining pure isolates from samples believed to contain any number of microorganisms are well known to those with skill in the art and are not further described herein.

Basic methods for confirming a bacterial isolate as vancomycin resistant are well known to those skilled in the art and are not further described here. (See for example the recommendations provided by the Clinical and Laboratory Standards Institute (CLSI)). These susceptibility methods require a pure isolate and therefore cannot be performed directly on a clinical (biological) sample.

While the basic methods for screening a clinical sample for VRE provide little to no identification at either the genus or species level, the incorporation of esculin into the vancomycin-containing base medium can provide a presumptive identification at the genus level (i.e., *Enterococcus*) because all enterococci hydrolyze esculin and, in the presence of ferric citrate, produce a brown to black colony. These types of media are commercially available (from, for example, BD Diagnostic Systems, Sparks, Md.) and include Enterococcal Agar with Vancomycin and Bile Esculin Azide Agar with Vancomycin.

Broth media containing esculin have also been used to screen for VRE. Like the screen plates, these media are also commercially available (e.g., enterococci broth and VRE broth), and offer only a presumptive identification at the genus level.

Another method for detecting VRE utilizes CHROMagar Orientation (CHROMagar Company, Paris). Unmodified CHROMagar Orientation contains two chromogenic substrates, beta-D-glucopyranoside and beta-D-galactopyranoside. In order to make it useful in screening for VRE, CHROMagar Orientation was modified by adding sodium azide and vancomycin. Beta-D-glucopyranoside is a substrate that is hydrolyzed by almost all species of enterococci. Beta-D-galactopyranoside, while in some environments is hydrolyzed specifically by *E. faecium*, is not hydrolyzed or minimally hydrolyzed in the presence of beta-D-glucopyranoside. Although modified CHROMagar Orientation can distinguish between various bacterial genera (e.g., *Enterococcus* from *Escherichia*), it cannot differentiate among the species of enterococci, and therefore, cannot differentiate among the clinically significant species containing the vanA and vanB genes.

Chen et al. (U.S. Pat. Nos. 5,620,865, 6,355,449 and 7,018,807) describes a medium for the detection of VRE utilizing a basic medium for the detection of vancomycin-resistance to which nutrient indicators specific for enterococci have been added. However, the nutrient indicators suggested in the Chen patents are universal for *Enterococcus* and thus provide only for detection at the genus level and not the species level.

Other media, which are not intended for direct screening of specimens, have also been evaluated (e.g., Campylobacter Agar and Vancomycin Screen Agar). These media are selective and facilitate the recovery of VRE however; they cannot offer identification at either the genus or the species level. In order to do so, further testing, including Gram stain and pyrrolidonyl arylamidase (the PYR test) are often used. In addition, once the organism has been presumptively identified as an *Enterococcus* species, further tests such as those for motility or acidification, are needed to distinguish *E. casseliflavus* and *E. gallinarum* from *E. faecium* and *E. faecalis*.

Molecular methods such as polymerase chain reaction (PCR) and cycling probe technology are available for the detection of vancomycin resistance genes. These methods offer a high degree of sensitivity and specificity as well as decreased turn around time compared to routine culture. However, they often only detect the van genes and do not provide a species level identification. In addition, many laboratories do not have the facilities, training or volume to justify performing such costly, complex procedures.

Identification (ID) to the species level can be accomplished using a commercially available automated or manual ID system, although it has been noted that some of the commercial systems may not always accurately identify *E. faecium*. All of these systems require a pure isolate and can take up to 24 hours to obtain a definitive identification. Automated systems such as Phoenix (BD Diagnostic Systems), Vitek (bioMerieux) and Microscan (Dade) provide a species level identification in 2-24 hours. Manual systems such as Crystal (BD Diagnostic Systems) and API/ATB (bioMerieux) will also provide a definitive species level identification in 4-24 hours.

Other methods include a chemiluminescence vancomycin and teicoplanin Minimum Inhibitory Concentration (MIC) assay (Eiken Chemicals). According to a study by Nagasawa, et al., this chemiluminescence assay can differentiate vanA, vanB and vanC isolates, based on their MICs, in 2-4 hours. Another MIC method, that employs resazurin as a growth indicator, can be used to rapidly determine the susceptibilities to vancomycin. However, both of these susceptibility test methods require a pure isolate and thus are not suitable for use with the original patient sample.

As previously discussed, current methods for detecting and identifying VRE at the species level require either a pure isolate and or multiple tests. Thus, a method for speciating enterococci rather than providing a genus level identification from the original patient specimen is desired.

SUMMARY OF THE INVENTION

The present invention is a method and medium for differentiating between two species of microorganisms present in a biological sample. The medium (i.e. a solid or liquid and growth components) has at least two substrates. The first substrate is selective for a first enzyme over a second enzyme. The second substrate is selective for a second enzyme over the first enzyme. The first enzyme is produced by a first species of microorganism and the second enzyme is produced by a second species of microorganism.

The first and second substrates are each conjugated with a moiety that images when cleaved from the substrate. "Images" as used herein means an observable effect. Examples of observable effects include the release of a color or fluorescence. In preferred embodiments herein, the moieties are chromogens.

In one embodiment, the medium allows for the detection of VRE directly from a biological sample, within as little as 24 hours. The medium facilitates the direct identification and differentiation among two or more species of VRE (e.g., *E. faecium* from *E. faecalis*) within the sample without resorting to additional testing procedures. The medium provides a vehicle for detecting VRE generally and certain species of VRE specifically (e.g., *E. faecium*, *E. faecalis*, and *E. gallinarum/E. casseliflavus*) from a biological sample using a single testing procedure.

In certain embodiments the growth components are amino acids, vitamins, salt and trace elements in amounts sufficient to allow viability and reproduction of enterococci in the presence of a plurality of substrates. A first substrate is specific for an enzyme produced by a first species of enterococci. A second substrate is specific for an enzyme produced by a second species of enterococci. It is advantageous if at least two of the substrates are conjugated with a chromogenic species. The substrate conjugated to the chromogenic species is referred to as a chromogenic substrate herein. The chromogenic substrates are provided in an amount sufficient to allow a detectable characteristic signal to be produced in the medium by the growth of the *Enterococcus* species specific for the chromogenic substrate. The medium further contains effective amounts of selective agents, which prevent or inhibit the growth of non-target (i.e., non-enterococcal) microorganisms. In the embodiment of the present invention wherein the media is selective for VRE, the selective agent is at least vancomycin. In an alternate embodiment, the selective agents are at least a combination of vancomycin and cefoxitin. In other embodiments, selective agents include a combination of vancomycin and other selective agents that will select out non-target organisms that might otherwise "break through" and grow and yield a false positive. In one embodiment, the selective agent is erythromycin. Erythromycin prevents lactobacilli from growing in the media. Left unselected, a *Lactobacillus* colony could grow and yield a false indication that VRE is present in the sample. The invention contemplates many different selective agents in addition to vancomycin and cefoxitin.

The invention contemplates a method wherein differentiation between at least two species of enterococci is accomplished in one container in a single step. In the method, a biological sample is obtained. For VRE, that sample is often a rectal swab. In this embodiment, a VRE-selective media is provided. As such, vancomycin is one media constituent. In one embodiment the media is agar with nutrients to support such growth and selective agents to suppress the growth of non-VRE organisms. The media optionally contains additional antibiotics to suppress or eliminate the growth of non-target organisms that may grow in the presence of vancomycin. The media also contains at least two substrates that select for enzymes produced by the target organisms as described above. The media is then exposed to conditions that cause the target organisms to grow. The media is then directly inspected for an indication of the presence of one or more species of VRE, without subjecting the media to any additional testing.

DETAILED DESCRIPTION

Figure 1:
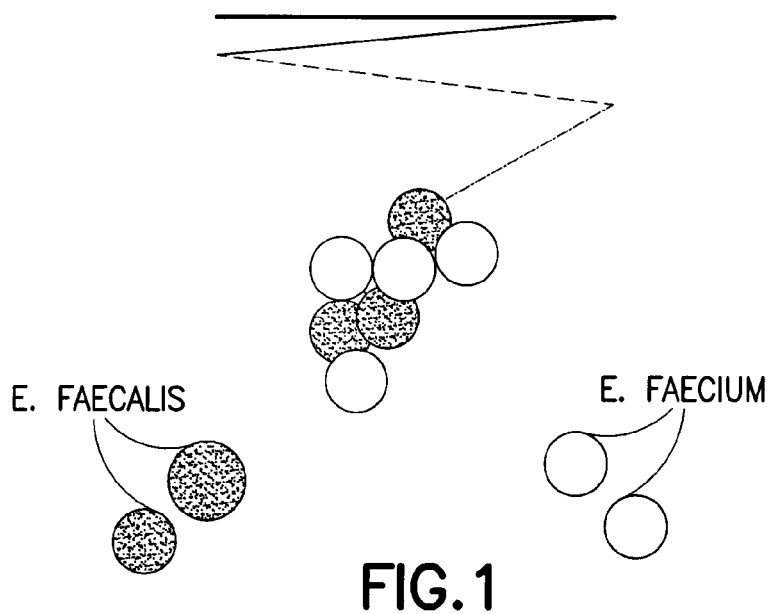
FIG. 1 depicts an agar plate wherein two distinct colony colors, identifying two different species of VRE, are visualized.

The following definitions are employed for purposes of this disclosure.

As used herein, the term "medium" (plural "media") refers to a solid, semi-solid, powder or liquid mixture, which contains all or substantially all of the components necessary to allow a microbe to grow and reproduce. The medium may be sterile or non-sterile as generally accepted practice requires.

As used herein, the term "biological sample" refers to any sample taken from or coming from a substance that might be expected to contain bacteria and/or other microorganisms, and includes, but is not limited to, samples from the environment (e.g., soil or water), or samples from humans (e.g., clinical samples such as stool, rectal swabs, urine, blood, wounds).

As used herein, the term microorganism refers to microscopic organisms and include, but is not limited to, bacteria, fungi, yeasts, molds and viruses.

As used herein, the term "streak" refers to the act of introducing a sample to the surface of an agar plate by means of dragging a suitable tool (such as an inoculation loop) across the surface of the agar plate.

As used herein, the term "effective amount of nutrient" refers to an amount within the range which allows or promotes growth and reproduction of a target microorganism. That is, an amount which allows the microbes or other organisms to adapt to the medium, synthesize the necessary constituents for reproduction and subsequently reproduce.

As used herein, the term "effective amount of substrate" refers to the amount of substrate required to achieve the desired effect without interfering with the desired activity of other substrates that may be present in the medium.

The terms "vitamins", "amino acids", "trace elements" and "salts" are meant to include all molecules, compounds and substances (substances hereinafter) classified in each category by those of skill in the art whether organic or inorganic, and the categories are without regard to whether or not such substances are necessary for or conducive to maintaining life.

As used herein, the term "imaging moiety" refers to a moiety that, when activated, provides a detectable signal such as a color change, fluorescence or a change in pH.

As used herein, the term chromogenic substrate or chromogen refers to a substrate conjugated to a chromophore. When cleaved from a substrate, the chromophore becomes oxidized and produces a visible color. Similarly a fluorogenic substrate or fluorogen refers to a substrate coupled to a fluorophore. A fluorophore, as the name indicates, provides a fluorescent signal. The use of fluorogenic substrates in the present invention are also contemplated as suitable.

As used herein, the term "inducer substrate" refers to a substrate capable of inducing the expression of an enzyme or enzymes that would otherwise remain unexpressed.

As used herein, the term "detectable characteristic signal" refers to any change in a sample which may be detected by one or more of the human senses. The term includes such examples as color change in the visible or non-visible wavelength ranges, a change in state such as between solid, liquid and gas, an emission of gas, or a change in odor.

As used herein, the term "target microbe" refers to the microorganism whose presence or absence is sought to be detected.

The medium described herein allows for the species-level detection and identification of VRE by providing chromogenic substrates in a medium capable of supporting the growth of a plurality of species of VRE. The medium inhibits the growth of non-VRE organisms and, optionally, some species of VRE organisms.

Generally, a medium capable of supporting the growth of microbes contains a variety of components. At a minimum, such media should include amino acids, salts, vitamins, a carbon source and other inorganic moieties. Amino acids are available from a variety of sources including natural sources (e.g., digests of animal tissue). They may be provided as mixtures or in purified form. Mixtures of amino acids obtained from natural sources often contain varying amounts of each amino acid. Not all amino acids must be provided, and the relative amount can vary. The following provides a list of medium constituents and their amounts, offered as guidance and not as a limitation.

In one embodiment, the medium may contain at least the following amino acids in approximately the following amounts (grams per liter of medium {G/L}): alanine (about 0.1 to about 0.3 G/L), arginine (about 0.1 to about 0.3 G/L), aspartic acid (about 0.4 to about 0.7 G/L), cystine (about 0.01 to about 0.015 G/L), glutamic acid (about 1.0 to about 1.6 G/L), glycine (about 0.12 to about 0.17 G/L), histidine (about 0.116 to about 0.17 G/L), isoleucine (about 0.25 to about 0.37 G/L), leucine (about 0.4 to about 0.6 G/L), lysine (about 0.37 to about 0.56 G/L), methionine (about 0.13 to about 0.19 G/L), phenylalanine (about 0.2 to about 0.3 G/L), proline (about 0.4 to about 0.6 G/L), serine (about 0.18 to about 0.26 G/L), threonine (about 0.19 to about 0.28 G/L), trytophan (about 0.05 to about G/L 0.07), tyrosine (about 0.12 to about 0.18 G/L), and valine (about 0.29 to about 0.44 G/L).

Salts may be provided in the medium as a source of ions upon dissociation. Such salts may include (per L of medium): potassium chloride (about 0.5 to about 1.5 G), copper sulfate (about 40 to about 50 microgram (µG)), ammonium sulfate (about 4.0 to about 6.0 G), potassium iodide (about 50 to about 150 µG), manganese sulfate (about 300 to about 500 µG), sodium molybdate (about 150 to about 250 µG), zinc sulfate (about 300 to about 500 µG), and sodium chloride (about 0.05 to about 0.15 G).

Vitamins required for growth and reproduction of the microorganism sought to be detected may also be provided. These can be provided in purified form or as mixtures. Such vitamins may include (per L of medium): biotin (about 220 to about 330 µG), pantothenic acid (about 44 to about 66 µG), pyridoxine (about 9 to about 14 milligram (mG)), riboflavin (about 11 to about 17 mG), folic acid (about 6 to about 8 mG), thiamine (about 16 to 24 mG), niacin (about 15 to 23 mG), and trace amounts (less than about 10 µg) of cyanocobalamin.

A carbon source may also be provided. Sugar may be provided as the carbon source, examples of which include (G/L): dextrose (about 0.1 to about 10), sucrose (about 0.1 to about 10), maltose (about 0.1 to about 10), lactose (about 0.1 to about 10), xylose (about 0.1 to about 10), galactose (about 0.1 to about 10) and starch (about 0.1 to about 10). Other nutrients include peptones such as casein peptones, soy peptones and meat peptones.

The media can optionally include other inorganic substances to aid in microbial growth. These include (to the extent not already provided in the above sources, per L of medium): Phosphorus (about 0.5 mG), potassium (about 0.4 mG), sodium (about 30 to about 60 mG), and trace amounts (less than about 10 µg) of calcium, magnesium, aluminum, barium, chloride, cobalt, copper, iron, lead manganese, sulfate, sulfur, tin and zinc.

In addition to components that promote the growth of target microbes, components that inhibit the growth of non-target microbes (and therefore cause the media to select for VRE) may also be included. These components differentiate between the target organisms (e.g. vanA- and vanB-containing enterococci) and non-target organisms (i.e. non VRE organisms) For example, and not by way of limitation, (in G/L), Colistin (about 0.005 to about 0.04), Nalidixic acid (about 0.003 to about 0.01), and Amphotericin B (about 0.006 to about 0.02) may be added in addition to vancomycin which is present in an exemplary concentration of about 0.004 to about 0.016 G/L to inhibit or prevent the growth of non-enterococci and vancomycin-sensitive enterococci in the medium. Preferably, the medium has a vancomycin concentration of about 0.006 to about 0.01 G/L. Non-target microbes that might interact with the substrates in the media to produce an observable effect (such as a color) that is similar to the color produced by the interaction of the VRE with the chromogenic substrates in the media are of particular concern. Lactobacilli, if present, will interact with the substrates in the media and the colony will have a color similar to the color of a target VRE species. Therefore, it is advantageous if the media contains an amount of erythromycin (about 0.0001 to about 0.01 G/L) that suppresses the growth of lactobacilli but does not adversely affect the growth of the target organisms or the species-differentiation of the target organisms in the media.

The embodiment in Table 1 below also includes a cephalosporin (e.g. cefoxitin). The cefoxitin, in combination with the vancomycin, will selectively inhibit vanC containing strains, leaving the vanA and vanB containing strains to be distinguished from each other based upon the selective interaction of each with their respective chromogenic substrate. In certain settings, it is preferred to suppress the growth of the vanC-containing strains, rather than allowing the vanC-containing strains to grow in an environment where they can be distinguished from the vanA- and vanB-containing strains. Cefoxitin is present in an amount of about 0.002 g/l to about 0.04 g/l to accomplish this objective. Preferably, Cefoxitin is present in an amount of about 0.004 g/l to about 0.02 g/l to accomplish this objective.

Media may be provided in several forms including, e.g., solids, powders (rehydrated prior to use), semi-solids (e.g., agar-based medium) or liquids (e.g., broth).

In one illustrative embodiment, and not by limitation, a semi-solid medium, suitable for promoting the growth of VRE while suppressing the growth of non-VRE (including genera other than *Enterococcus*) is described in Table 1 below.

TABLE 1

| Component | Amount (G/L) |
|---|---|
| A. Supporting the growth of VRE | |
| casein peptone | about 5 to about 30 |
| Magnesium sulfate | about 0.4 |
| Sodium chloride | about 3.95 |
| Agar | about 13.45 |
| Dextrose | about 1.05 |
| Beef extract | about 0.25 |
| soy peptone | about 5 to about 25 |
| Soluble starch | about 0.5 |
| Yeast extract | about 0.075 |

TABLE 1-continued

| Component | Amount (G/L) |
|---|---|
| Sodium pyruvate | about |
| meat peptone | about 10 to about 25 |
| Sodium phosphate dibasic | about 1.3 |
| B. Inhibiting the growth of non-VRE organisms | |
| Vancomycin | about 0.004 to about 0.016 |
| Colistin | about 0.005 to about 0.04 |
| Nalidixic acid | about 0.003 to about 0.01 |
| Amphotericin B | about 0.006 to about 0.02 |
| Cefoxitin | about 0.004 to about 0.02 |

The formulation described above is provided for illustrative purposes. One skilled in the art will recognize that there are many suitable alternatives for the specific components enumerated in the table above. For example, Polymyxin B (in a concentration of about 0.012 to about 0.075 G/L) and aztreonam (in a concentration of about 0.005 to about 0.1 G/L), are contemplated as examples of alternatives to colistin and nalidixic acid, respectively, in the medium. However, in certain preferred embodiments aztreonam is present in addition to colistin, nalidixic acid and the other components that inhibit the growth of the non-VRE organisms. Polymyxin B and aztreonam are capable of performing the same function (i.e. suppressing gram-negative rods) in the medium as colistin and nalidixic acid. However, polymyxin B, as an alternative, is currently somewhat less preferred, from a manufacturing and stability perspective, than colistin and nalidixic acid. Another antibiotic contemplated for suppressing the growth of non-VRE organisms (e.g. *Lactobacillus*) is erythromycin. While many antibiotics are know to suppress the growth of *Lactobacillus*, (e.g. clindamycin), erythromycin does so without inhibiting or otherwise adversely affecting the growth of the VRE in the media.

Those skilled in the art will appreciate that not every component is required. Components may be substituted with other components of similar properties. The amounts of the components may also be varied. Further, although Table 1, the preceding discussion and the following examples describe the invention in terms of VRE, it is to be understood that, with appropriate variations of the components in the medium and proper selection of chromogenic substrates, one skilled in the art would be able to detect and identify other microorganisms at the species level. For example, one skilled in the art could alter the media to be more suitable for the growth of *Staphylococcus* and thus be able to detect vancomycin resistant *Staphylococcus aureus*

While the medium described in Table 1 is capable of detecting the presence of VRE, it cannot identify what organism is present. In order to differentiate between species of VRE in a biological sample, chromogenic substrates specific and unique for the target bacteria must be added. Thus, the medium described herein has specific chromogenic substrates added thereto. Chromogenic substrates are well known to those skilled in the art and are commercially available.

Chromogenic substrates, as described herein, have two basic constituents: i) the substrate (e.g., nominally alpha-D-glucopyranoside); and ii) a chromophore conjugated to the substrate. The substrates described herein are specific examples of a large class of known chromogenic substrates generally referred to as indolyl substrates). One skilled in the art is aware that such indolyl substrates are commercially available. A chromogen, as used herein is a substance that is capable of conversion into a pigment. Specific enzymes hydrolyze specific substrates. Upon hydrolysis, the chromophore is released from the substrate and produces a characteristic signal (e.g., displays a distinct color). As previously noted, whether or not a chromogenic substrate will be hydrolyzed and the chromophore released is affected by several factors. One factor is the presence of other substrates. For example beta-D-galactopyranoside is either not hydrolyzed or less hydrolyzed by enterococcal species when beta-D-glucopyranoside is present. Also, not all chromogens will display their characteristic signal in the presence of other chromogens (e.g., certain fluorescent chromophores will quench the fluorescence of other chromophores when both are simultaneously expressed). Many substrates are not species specific but instead are genus specific, for example esculin and PYR are genus specific for *Enterococcus* but do not speciate within the genus. Thus, the selection and amount of any such chromogenic substrate is critical to the ultimate identification of VRE at the species level.

Although not wishing to be bound to a particular theory, Applicant believes that identification of two or more species of VRE is accomplished with the inventive medium because specific VRE produce species-specific enzymes, either naturally or induced. Each species-associated enzyme is specific for a substrate in the media. Said substrates are conjugated to different chromophores, selected for their ability to be visually perceived simultaneously. When the VRE produced enzyme selectively interacts with its specific substrate, the chromophore conjugated to said substrate is released, and its visually detectable characteristic signal is produced. As previously noted, the characteristic signal is discernable even if other chromogens image simultaneously.

In one embodiment of the present invention, the media contains two chromogenic substrates. The first substrate is specific for an enzyme that is produced by one species of microorganism and the second substrate is specific for an enzyme produces by a different species of microorganism. In this embodiment, both species of microorganism are collectively the target microbes. Alpha-D-glucosidase and beta-D-galactosidase are the enzymes produced by these microbes. Each target microbe selectively hydrolyzes the respective chromogenic substrate in the medium to yield a distinctive, detectable signal.

One skilled in the art will appreciate that the observed effect (i.e., the color change) associated with the enzyme-specific hydrolysis of the chromogenic substrate is local. By local it is meant that the color change will occur in that region of the substrate where the species of microbe that produces that enzyme is located. If two species are located close together, both will image because the chromogenic substrates are selected to ensure that each chromogen will image independently even if imaging proximate to the other chromogen. As previously noted, the color change may be within the visible wavelength range. For fluorogens, the signal is fluorescent and is therefore visible in a wavelength range after exposure to an excitation light source.

In an exemplary embodiment for selectively imaging the *E. faecium* and *E. faecalis* species of enterococci, the chromogenic substrates provided in the media are an indolyl-beta D-galactopyranoside and an indolyl-alpha D-glucopyranoside (chromogenic substrates are commercially available from a variety of suppliers). The resulting medium will not only indicate the presence of VRE, but will also visually distinguish between *E. faecalis* and *E. faecium* if both species are present. If only one of *E. faecalis* or *E. faecium* is present, the color exhibited by the medium and or colony, if any, will indicate, which of *E. faecalis* or *E. faecium* is present.

Figure 3:
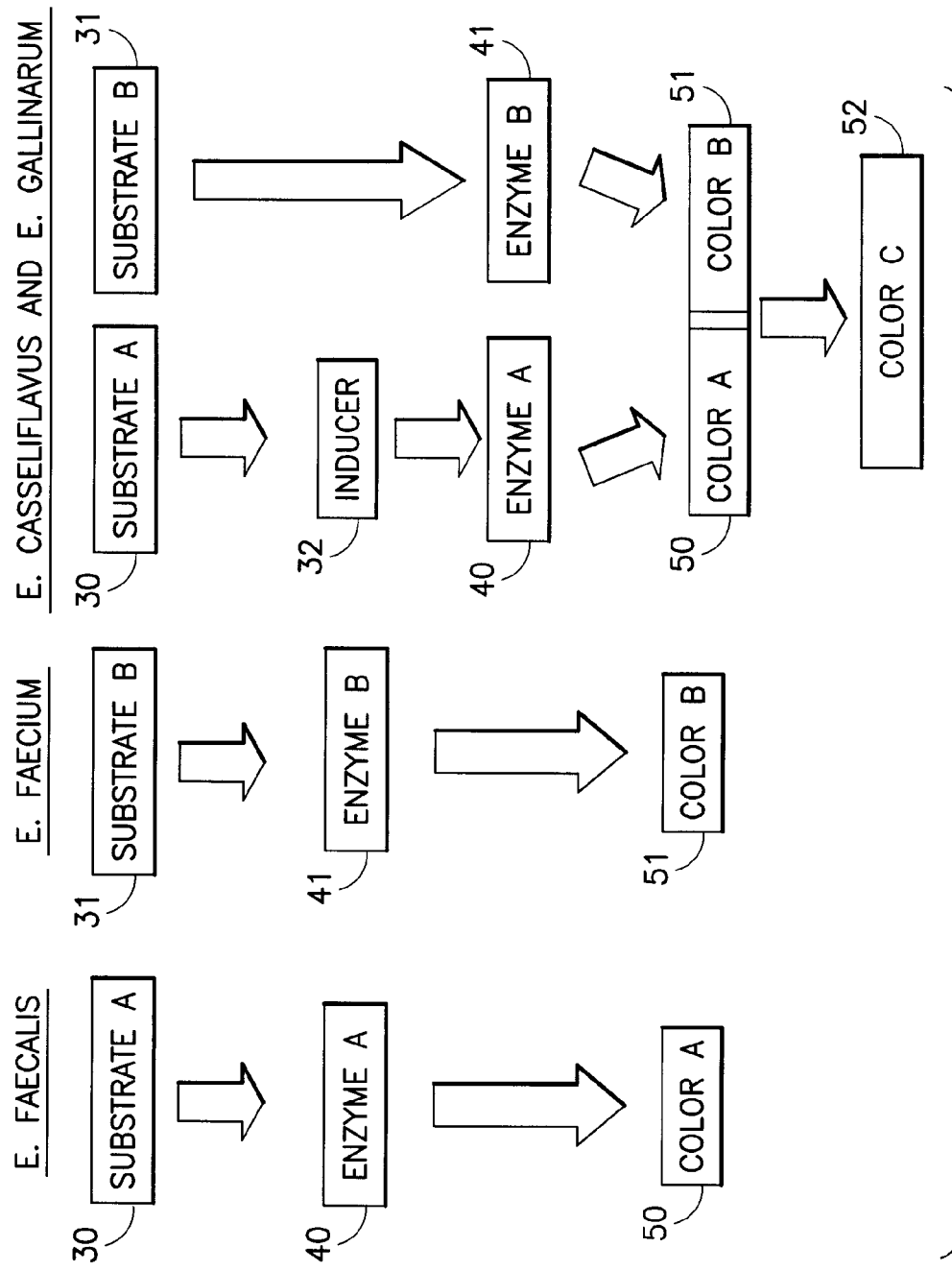
FIG. 3 is a flow chart depicting one embodiment of the present invention that distinctly images and differentiates three species of VRE.

In another embodiment, two chromogenic substrates and a third substrate are added to the VRE specific medium. Referring to FIG. 3, in this embodiment, each substrate (nominally substrate A (30), substrate B (31) and inducer (32)) interacts specific with certain enzymes (enzyme A (41), enzyme B (42) produced by different species of enterococci (*E. faecalis, E. faecium*, and *E. gallinarum/E. casseliflavus* in FIG. 3), such that the visualization of the chromogenic moieties does not interfere with each other. In this embodiment, the third (inducer) substrate 32 induces production of an enzyme (enzyme A (41) in a third species of enterococci (e.g., *E. gallinarum* or *E. casseliflavus*). The third substrate 32 does not have a chromogen attached thereto. It is for this reason that this third substrate, in this embodiment, is referred to as an inducer substrate.

Figure 2:
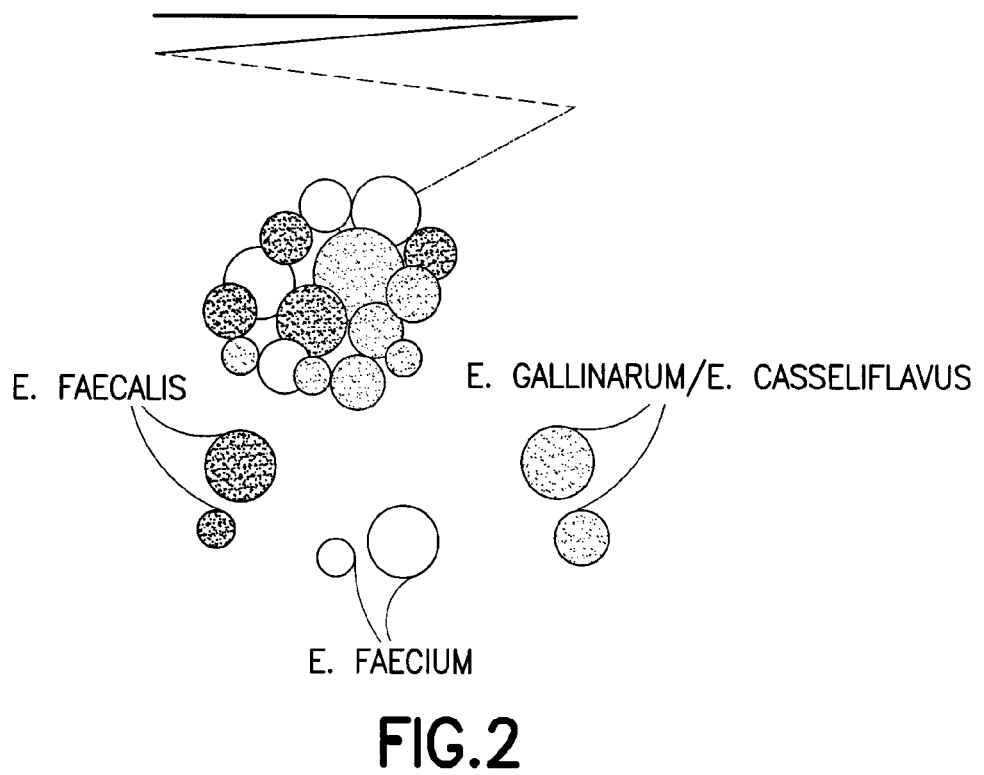
FIG. 2 depicts an agar plate wherein three distinct colony colors, identifying three different species of VRE, are visualized.

In an exemplary embodiment, the enterococci species that the substrates identify are the previously mentioned species of vancomycin-resistant enterococci (i.e., distinguishing *E. faecalis* from *E. faecium* from *E. gallinarum/E. casseliflavus*). The chromogenic substrates are indoxyl-beta D-galactopyranoside (Mag B gal) and indolyl-alpha D-glucopyranoside (X-alpha glu). As previously noted, these indolyl substrates are commercially available. The inducer substrate is methyl alpha-D-glucopyranoside (MGP). The inducer substrate 32 causes the species *E. gallinarum* and *E. casseliflavus* to produce enzyme A (41) in addition to enzyme B (42). Enzyme A hydrolyses indolyl-alpha D-glucopyranoside to produce color A (50). Since *E. casseliflavus* and *E. gallinarum* already produce the enzyme, beta-D-galactopyranosidase, substrate B (42) is also hydrolyzed. Consequently, if *E. faecalis* is present in this embodiment, the media will image a first color (50) of *E. faecalis* colonies. If *E. faecium* is present, the media will image a second color (51) of the *E. faecium* colonies. If *E. gallinarum* and/or *E. casseliflavus* are present, the media will image a third color (52) of the *E. gallinarum* and or the *E. casseliflavus* colonies. The third color (52) is a combination of the first (50) and second (51) colors. Referring to FIG. 2, the different colors (50, 51, and 52) for the three colonies (*E. faecalis, E. faecium* and *E. gallinarum* and/or *E. casseliflavus*) is illustrated.

The resulting medium will allow for the detection of VRE and the identification of at least three different, specific VRE species utilizing one sample and one test.

In yet another embodiment, two chromogenic substrates and cephalosporin (a class of a class of β-lactam antibiotics) are added to the VRE specific medium. In this embodiment, the combination of cephalosporin with vancomycin selectively inhibits vanC containing strains, leaving the vanA and vanB containing strains to be distinguished from each other based upon the selective interaction of each with their respective chromogenic substrate.

In an exemplary embodiment, the enterococci species that the chromogenic substrates are selected to identify are the previously mentioned species of vancomycin-resistant enterococci (i.e., *E. faecalis* and *E. faecium*). The chromogenic substrates are indolyl-beta D-galactopyranoside and indolyl-alpha D-glucopyranoside. The cephalosporin is cefoxitin. Cefoxitin is commercially available from a variety of sources. If *E. faecium* is present, the media images a first color of *E. faecium* colonies. If *E. faecalis* is present, the media will image a second color of the *E. faecalis* colonies. The growth of vanC containing organisms (*E. gallinarum* and/or *E. casseliflavus*) is inhibited by the presence of the cephalosporin (e.g. cefoxitin) in combination with the vancomycin.

The invention as described above in terms of certain embodiments is further understood with reference to the following examples.

FIG. 1 depicts a streak plate wherein two distinct colony colors can be seen. A mixed sample containing *E. faecium* and *E. faecalis* was streaked onto a screening plate comprised of the medium described in Table 1 to which the chromogenic substrates (indolyl-beta-D-galactopyranoside and indolyl-alpha-D-glucopyranoside) were added (0.2 and 0.1 G/L, respectively). The mauve colored colonies that were obtained indicated the hydrolysis of indolyl-beta-D-galactopyranoside by *E. faecium* while the green colonies that were obtained indicated the hydrolysis of indolyl-alpha-D-glucopyranoside by *E. faecalis*.

FIG. 2 depicts a streak plate wherein three distinct colony colors were observed. A mixed sample containing *E. faecium, E. faecalis* and *E. gallinarum/E. casseliflavus* was streaked onto a screening plate comprised of the medium described in Table 1 to which the chromogenic substrates, indolyl-beta-D-galactopyranoside and indolyl-alpha-D-glucopyranoside, and the inducer substrate MGP had been added ((0.2, 0.1 and 5.0 G/L, respectively). As in FIG. 1, the mauve colored colonies indicate the hydrolysis of indolyl-beta-D-galactopyranoside by *E. faecium* while the green colonies indicate the hydrolysis of indolyl-alpha-D-glucopyranoside by *E. faecalis*. The blue colored colonies indicate the hydrolysis of both indolyl-beta-D-galactopyranoside and indolyl-alpha-D-glucopyranoside by *E. casseliflavus* and *E. gallinarum*. FIG. 2 demonstrates how the epidemiologically important Enterococcal species, *E. faecium* and *E. faecalis*, can be distinguished from the epidemiologically insignificant Enterococcal species, *E. casseliflavus* and *E. gallinarum*.

In an alternate embodiment, a semi-solid medium, suitable for promoting the growth of VRE while suppressing the growth of non-VRE (including genera other than *Enterococcus*) is described in Table 2 below.

TABLE 2

| Component | Amount (g/l) |
|---|---|
| A. Supporting the growth of VRE | |
| casein peptone | about 5 to about 30 |
| Magnesium sulfate | about 0.4 |
| Sodium chloride | about 3.95 |
| Sexetam agar | 13.45 |
| Dextrose | 1.05 |
| Beef extract | 0.25 |
| soy peptone | about 5 to about 25 |
| Soluble starch | about 0.5 |
| Yeast extract | about 0.075 |
| Sodium pyruvate | about 0.25 |
| meat peptone | about 10 to about 25 |
| Sodium phosphate dibasic | about 1.3 |
| B. Inhibiting the growth of non-VRE organisms | |
| Vancomycin | about 0.004 to about 0.016 |
| Aztreonam | about 0.001 to about 0.01 |
| Colistin | about 0.0005 to about 0.04 |
| Nalidixic acid | about 0.003 to about 0.01 |
| Amphotericin B | about 0.006 to about 0.2 |
| Erythromycin | about 0.0001 to about 0.01 |
| Cefoxitin | about 0.004 to about 0.02 |

This formulation contains the antibiotics aztreonam and erythromycin in addition to the inhibitors listed in Table 1.

Example 1

Vancomycin Titration and Addition with Cefoxitin

Media was prepared to evaluate the effect of increasing vancomycin concentration on the sensitivity of the vanA, vanB (i.e. *E. faecium* and *E. faecalis*), and vanC (i.e. *E. casseliflavus/E. gallinarum*) containing species of enterococci. Isolates of the target organisms of interest (*E. faecium, E. faecalis, E. casseliflavus* and *E. gallinarum*) were obtained. A suspension was prepared for each isolate that was equivalent to a McFarland 0.5 ($10^8$). The suspensions were diluted according to the guidelines in the Clinical Laboratory Standards Institute (CLSI) M22-A3 document.

Media as described in Table 3 below were prepared. A standard streak plate method for inoculation was used for sample isolation. Each isolate was inoculated onto each media formulation. The plates were then incubated in ambient air (35° C.) and observed after 24 hours of incubation.

TABLE 3

| Component | Amount (g) | | | | | | | |
|---|---|---|---|---|---|---|---|---|
| | A | B | C | D | E | F | G | H |
| A. Supporting the growth of VRE | | | | | | | | |
| casein peptone | 30 | 30 | 30 | 30 | 30 | 30 | 30 | 30 |
| Magnesium sulfate | 0.4 | 0.4 | 0.4 | 0.4 | 0.4 | 0.4 | 0.4 | 0.4 |
| Sodium chloride | 5 | 5 | 5 | 5 | 5 | 5 | 5 | 5 |
| Meat peptone | 10 | 10 | 10 | 10 | 10 | 10 | 10 | 10 |
| Sexetam agar | 13.5 | 13.5 | 13.5 | 13.5 | 13.5 | 13.5 | 13.5 | 13.5 |
| soy peptone | 6 | 6 | 6 | 6 | 6 | 6 | 6 | 6 |
| Soluble starch | 5 | 5 | 5 | 5 | 5 | 5 | 5 | 5 |
| Yeast extract | 2 | 2 | 2 | 2 | 2 | 2 | 2 | 2 |
| Sodium pyruvate | 0.2 | 0.2 | 0.2 | 0.2 | 0.2 | 0.2 | 0.2 | 0.2 |
| Brain heart infusion (BHI) | 5 | 5 | 5 | 5 | 5 | 5 | 5 | 5 |
| Sodium phosphate dibasic | 5 | 5 | 5 | 5 | 5 | 5 | 5 | 5 |

TABLE 3-continued

| Component | Amount (g) | | | | | | | |
|---|---|---|---|---|---|---|---|---|
| | A | B | C | D | E | F | G | H |
| B. Inhibiting the growth of non-VRE organisms | | | | | | | | |
| Vancomycin | 0.005 | 0.0055 | 0.006 | 0.01 | 0.013 | 0.016 | 0.005 | 0.005 |
| Colistin | 0.01 | 0.01 | 0.01 | 0.01 | 0.01 | 0.01 | 0.01 | 0.01 |
| Nalidixic acid | 0.003 | 0.003 | 0.003 | 0.003 | 0.003 | 0.003 | 0.003 | 0.006 |
| Amphotericin B | 0.01 | 0.01 | 0.01 | 0.01 | 0.01 | 0.01 | 0.01 | 0.01 |
| Cefoxitin | 0 | 0 | 0 | 0 | 0 | 0 | 0.006 | 0 |
| Aztreonam | 0.01 | 0.01 | 0.01 | 0.01 | 0.01 | 0.01 | 0.01 | 0.01 |
| C. Substrates | | | | | | | | |
| MGP | 3 | 3 | 3 | 3 | 3 | 3 | 3 | 3 |
| X-alpha glu | 0.12 | 0.12 | 0.12 | 0.12 | 0.12 | 0.12 | 0.12 | 0.12 |
| Mag B gal | 3 | 3 | 3 | 3 | 3 | 3 | 3 | 3 |
| D. Other | | | | | | | | |
| Water (ml) | 1000 | 1000 | 1000 | 1000 | 1000 | 1000 | 1000 | 1000 |

The various antibiotics were prepared as stock solutions. Appropriate dilutions were made from each stock solution to achieve the concentrations specified in the above table.

Formulation A, which contained 5 µg of vancomycin, was observed to have the most distinct (blue) color for the vanC-containing isolates. However, colonies of two strains of E. gallinarum had a green color. There was some difficulty in distinguishing the green color produced by these two strains of the E. gallinarum species from the green color for the E. faecalis species in this formulation. Increasing the concentration of vancomycin caused the medium to lose sensitivity in the recovery of vanA and vanB isolates.

Sample G yielded a surprising result. While isolates of E. faecalis and E. faecium were recovered on the media, 8 of the 10 isolates of the vanC-containing species were suppressed. Sample G was the only sample that contained the antibiotic cefoxitin.

Example 2

Vancomycin-Cephalosporin Synergy Testing

In order to better understand the effect of cefoxitin on the vanC isolates, media having different cephalosporins with and without vancomycin were evaluated. The cephalosporins tested represented each of the four generations: cephalothin (1st gen.), cefoxitin (2nd gen.), cefotaxime (3rd gen.), and cefipime (4th gen.). Media containing penicillin with and without vancomycin were also evaluated.

The formulations for the evaluated media are presented in Table 4 below. Isolates of interest (primarily vanA, vanB, and vanC containing enterococci) were obtained. Each isolate was inoculated onto each media formulation. The plates were then incubated in ambient air (35° C.) and observed after 24 hours of incubation.

TABLE 4

| Components | Amounts (g/L) | | | | | | | | | | |
|---|---|---|---|---|---|---|---|---|---|---|---|
| | 1 | 2 | 3 | 4 | 5 | 6 | 7 | 8 | 9 | 10 | 11 |
| casein peptone | 30 | 30 | 30 | 30 | 30 | 30 | 30 | 30 | 30 | 30 | 30 |
| BHI | 5 | 5 | 5 | 5 | 5 | 5 | 5 | 5 | 5 | 5 | 5 |
| meat peptone | 10 | 10 | 10 | 10 | 10 | 10 | 10 | 10 | 10 | 10 | 10 |
| Yeast Extract | 2 | 2 | 2 | 2 | 2 | 2 | 2 | 2 | 2 | 2 | 2 |
| soy peptone | 6 | 6 | 6 | 6 | 6 | 6 | 6 | 6 | 6 | 6 | 6 |
| Sexetam Agar | 13.5 | 13.5 | 13.5 | 13.5 | 13.5 | 13.5 | 13.5 | 13.5 | 13.5 | 13.5 | 13.5 |
| Soluble Starch | 5 | 5 | 5 | 5 | 5 | 5 | 5 | 5 | 5 | 5 | 5 |
| Potassium Phosphate | 5 | 5 | 5 | 5 | 5 | 5 | 5 | 5 | 5 | 5 | 5 |
| Magnesium Sulfate | 0.4 | 0.4 | 0.4 | 0.4 | 0.4 | 0.4 | 0.4 | 0.4 | 0.4 | 0.4 | 0.4 |
| Sodium Chloride | 5 | 5 | 5 | 5 | 5 | 5 | 5 | 5 | 5 | 5 | 5 |
| Sodium Pyruvate | 0.2 | 0.2 | 0.2 | 0.2 | 0.2 | 0.2 | 0.2 | 0.2 | 0.2 | 0.2 | 0.2 |
| MGP | 3 | 3 | 3 | 3 | 3 | 3 | 3 | 3 | 3 | 3 | 3 |
| X-alpha-glu | 0.12 | 0.12 | 0.12 | 0.12 | 0.12 | 0.12 | 0.12 | 0.12 | 0.12 | 0.12 | 0.12 |
| Mag-B-Gal | 0.3 | 0.3 | 0.3 | 0.3 | 0.3 | 0.3 | 0.3 | 0.3 | 0.3 | 0.3 | 0.3 |
| Vancomycin | 0.006 | | | | | | 0.006 | 0.006 | 0.006 | 0.006 | 0.006 |
| Amphotericin B | 0.01 | 0.01 | 0.01 | 0.01 | 0.01 | 0.01 | 0.01 | 0.01 | 0.01 | 0.01 | 0.01 |
| Nalidixic acid | 0.006 | 0.006 | 0.006 | 0.006 | 0.006 | 0.006 | 0.006 | 0.006 | 0.006 | 0.006 | 0.006 |
| Colistin | 0.02 | 0.02 | 0.02 | 0.02 | 0.02 | 0.02 | 0.02 | 0.02 | 0.02 | 0.02 | 0.02 |
| Cefoxitin | | 0.02 | | | | | | 0.02 | | | |

TABLE 4-continued

| Components | \multicolumn{11}{c}{Amounts (g/L)} | | | | | | | | | | |
| --- | --- | --- | --- | --- | --- | --- | --- | --- | --- | --- | --- |
| | 1 | 2 | 3 | 4 | 5 | 6 | 7 | 8 | 9 | 10 | 11 |
| Cefotaxime | | | 0.02 | | | | | 0.02 | | | |
| Cefipime | | | | 0.02 | | | | | 0.02 | | |
| Cephalothin | | | | | 0.02 | | | | | 0.02 | |
| Penicillin | | | | | | 0.02 | | | | | 0.02 |
| Water (amt. in ml) | 1000 | 1000 | 1000 | 1000 | 1000 | 1000 | 1000 | 1000 | 1000 | 1000 | 1000 |

The various antibiotics were prepared as stock solutions. Appropriate dilutions were made from each stock solution in order to achieve the final concentration as specified in the formulation.

Figure 4:
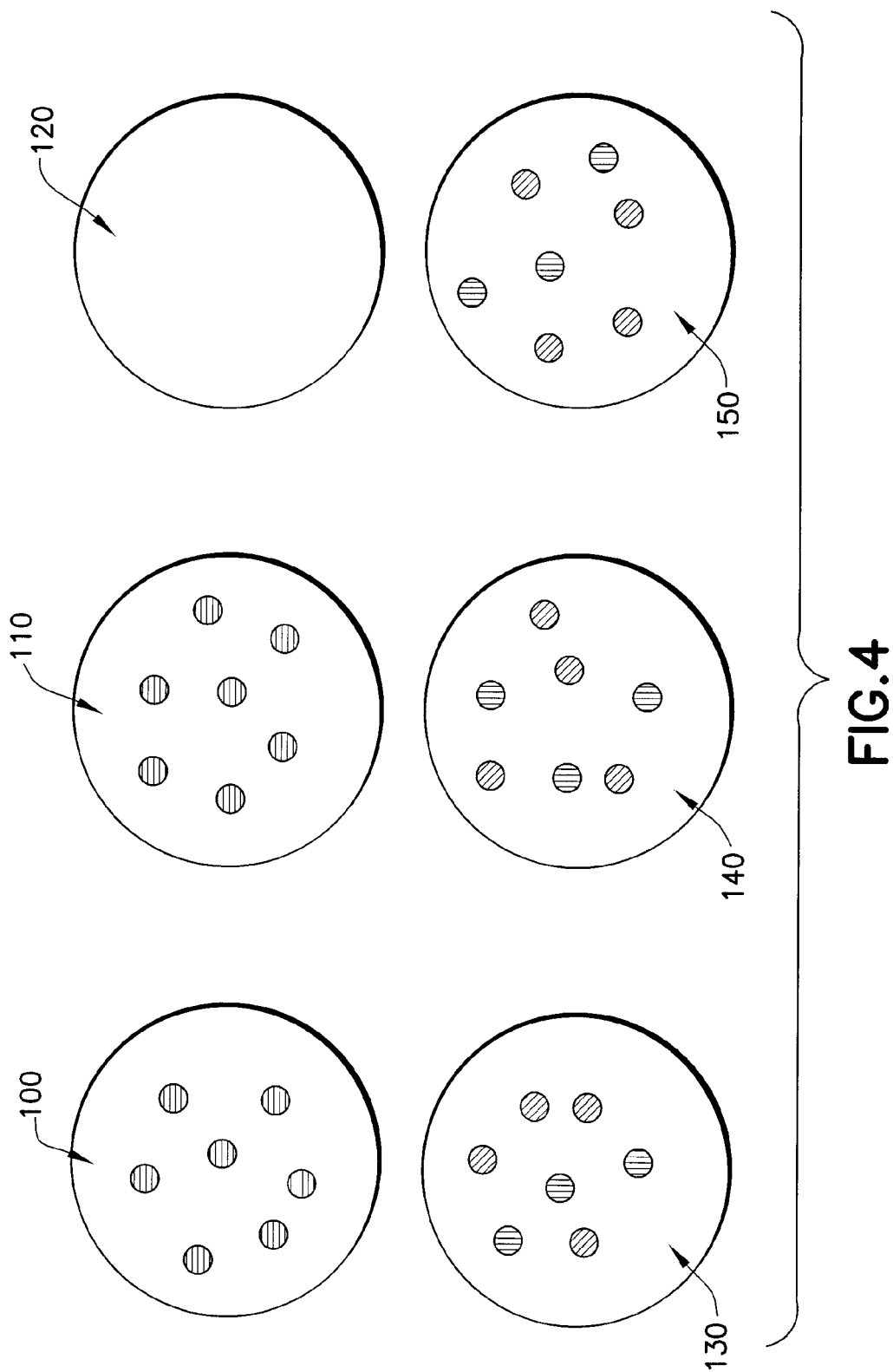
FIG. 4 compares colonies that image in agar plates having different formulations that select for VRE.

The media, upon incubation in Petri dishes as described above, was observed to determine what colonies developed and the color of those colonies. Some results are illustrated in FIG. 4. Specifically, dish 100, which contained formulation 1 above (vancomycin only), had bright blue colonies (indicated by horizontal cross hatching). This indicates that vanC-containing species of enterococci were not inhibited by the vancomycin in formulation 1. Similar results were observed in Petri dish 110 for formulation 2 (which did not contain vancomycin but did contain cefoxitin). This formulation did not inhibit the vanC-containing species of enterococci. Dish 120 contained formulation 7 (vancomycin and cefoxitin). The complete absence of blue colonies indicated that formulation 7 (the combination of vancomycin and cefoxitin with no other VRE inhibitors) completely inhibited vanC-containing enterococci.

The effect of formulations 1, 2, and 7 on vanA- and vanB-containing isolates is illustrated in dishes 130-150. Specifically, none of the formulations inhibited the growth of the vanA- and vanB-containing species. E. faecium colonies are indicated by the mauve (vertical cross-hatching) color. E. faecalis colonies are indicated by the green (diagonal cross-hatching) color. Consequently, the tested formulations with vancomycin alone, cefoxitin alone and a combination of cefoxitin and vancomycin were not observed to suppress or inhibit the growth of vanA- and vanB-containing enterococci.

The other cephalosporins tested, with vancomycin, did not produce the same effect as cefoxitin (inhibition of vanC-containing isolates while allowing recovery of vanA and vanB isolates). While they were observed (for the most part) to inhibit the vanC isolates, they were also observed to inhibit many of the vanA and vanB isolates.

Referring to formulations 6 and 11 (without and with vancomycin, respectively) the media containing penicillin was found to be too inhibitory, suppressing almost all of the isolates.

Although cefoxitin was the only cephalosporin that produced the desired results in this experiment, other cephalosporins in addition to cefoxitin, other than the ones tested, are contemplated as likely to produce acceptable inhibition of vanC isolates without inhibiting vanA and vanB isolates.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A medium for detecting and differentiating species of enterococci comprising:
   a first substrate conjugated to a first imaging moiety, wherein the first substrate preferentially interacts with a first enzyme that is produced by a first species of enterococci compared to a second enzyme that is produced by a second species of enterococci; and
   a second substrate conjugated to a second imaging moiety, wherein the second substrate preferentially interacts with the second enzyme that is produced by the second species of enterococci compared to the first enzyme that is produced by the first species of enterococci;
   an inhibitor of non-vancomycin resistant enterococci comprising vancomycin;
   a third substrate;
   and cefoxitin;
   wherein the third substrate, but not the first and second substrates, induces the production of the first enzyme by at least a third species of enterococci that produces the second enzyme without inducement;
   wherein the first imaging moiety images a first indicator when the first substrate interacts with the first enzyme and the second imaging moiety images a second indicator when the second substrate interacts with the second enzyme;
   and the combined presence of the first imaging moiety and second imaging moiety image a third indicator in the combined presence of the first enzyme and the second enzyme produced by the third species of enterococci,
   wherein the first, second and third indicators are perceptually different from each other;
   and wherein the cefoxitin in combination with vancomycin either inhibits the growth of the third species of enterococci but not the growth of the first or second species of enterococci or the third species of enterococci overcomes the inhibition wherein the third indicator indicates that the third species overcame the inhibition.

2. The medium of claim 1 wherein the first and second imaging moieties are selected from the group consisting of chromophores and fluorophores.

3. The medium of claim 2 wherein the first imaging moiety conjugated to the first substrate is a first chromogen and the second imaging moiety conjugated to the second substrate is a second chromogen.

4. The medium of claim 1, wherein the first substrate is alpha-D-glucopyranoside and the first enzyme is alpha-D-glucopyranosidase.

5. The medium of claim 1, wherein the second substrate is beta-D-galactopyranoside and the second enzyme is beta-D-galactopyranosidase.

6. The medium of claim 1, wherein the third substrate is methyl-alpha-D-glucopyranoside.

7. The medium of claim 1 wherein the first species of enterococci is a vancomycin resistant enterococci.

8. The medium of claim 7 wherein the vancomycin resistant enterococci is E. faecalis or E. faecium.

9. The medium of claim 1 wherein the second species of enterococci is a vancomycin resistant enterococci different from the first species.

10. The medium of claim 9 wherein the vancomycin resistant enterococci is E. faecalis or E. faecium and different from the first species.

11. The medium of claim 1 wherein the at least third species of enterococci is a third species of vancomycin resistant enterococci selected from the group consisting of E. casseliflavus, E. gallinarum and combinations thereof.

12. The medium of claim 1 wherein the inhibitor of non-vancomycin resistant enterococci further comprises an inhibitor selected from the group consisting of colistin, nalidixic acid, aztreonam, amphotericin B, and combinations thereof.

13. The medium of claim 1 wherein the inhibitor of non-vancomycin resistant enterococci further comprise erythromycin.

14. The medium of claim 1, wherein the production of the first enzyme by the third species of enterococci is normally repressed within the third species of enterococci until the third substrate is present and wherein the normally repressed enzyme interacts preferentially with the first substrate to image the first indicator.

15. The medium of claim 1 wherein the vancomycin is present in an amount effective to inhibit the growth of at least some non-vancomycin resistant enterococci and not significantly inhibit the growth of vancomycin resistant enterococci.

16. The medium of claim 1 wherein the cefoxitin is present in an amount effective to suppress the growth of the vanC-containing enterococci.

17. The medium of claim 1 wherein the amount of cefoxitin does not significantly suppress the growth of a vancomycin resistant enterococci selected from the group consisting of vancomycin resistant enterococci containing a vanA gene and vancomycin resistant enterococci containing a vanB gene.

18. The medium of claim 1 wherein the third substrate induces the first enzyme, wherein the first enzyme is alpha-D-glucopyranosidase.

* * * * *